(12) United States Patent
Latour (10) Patent No.: US 8,323,355 B2
(45) Date of Patent: Dec. 4, 2012

(54) ANCHORING SYSTEM FOR PROSTHETIC AND ORTHOTIC DEVICES

(75) Inventor: Debra Ann Latour, Springfield, MA (US)

(73) Assignee: Shriners Hospitals For Children, Tampa, FL (US)

(*) Notice: Subject to any disclaimer, the term of this patent is extended or adjusted under 35 U.S.C. 154(b) by 0 days.

(21) Appl. No.: 13/073,248

(22) Filed: Mar. 28, 2011

(65) Prior Publication Data

US 2011/0172787 A1   Jul. 14, 2011

Related U.S. Application Data

(63) Continuation of application No. 11/787,161, filed on Apr. 13, 2007, now abandoned.

(60) Provisional application No. 60/793,178, filed on Apr. 19, 2006.

(51) Int. Cl.
*A61F 2/54* (2006.01)
*A61F 5/01* (2006.01)

(52) U.S. Cl. .......... 623/63; 623/58; 623/57; 602/5; 602/20

(58) Field of Classification Search .......... 623/30, 623/31, 58, 61–63, 65; 602/5, 12, 20, 21
See application file for complete search history.

(56) References Cited

U.S. PATENT DOCUMENTS

| | | | |
|---|---|---|---|
| 805,598 A | 12/1905 | Stokes | |
| 1,206,753 A | 11/1916 | Desmore | |
| 2,542,316 A | 2/1951 | Farrar | |
| 2,668,959 A | 2/1954 | Sargeson | |
| 2,686,319 A | 8/1954 | Alderson | |
| 3,295,515 A * | 1/1967 | Kahn | 600/392 |
| 3,868,946 A * | 3/1975 | Hurley | 600/392 |
| 3,911,537 A * | 10/1975 | Mazur | 24/668 |
| 4,180,870 A | 1/1980 | Radulovic et al. | |
| 4,258,441 A | 3/1981 | Bell | |
| 4,291,421 A * | 9/1981 | Massey et al. | 623/63 |
| 4,685,925 A | 8/1987 | Childress et al. | |
| 5,206,957 A | 5/1993 | Gulick | |
| 5,400,782 A * | 3/1995 | Beaubiah | 600/394 |
| 5,651,792 A | 7/1997 | Telikicherla | |
| 5,800,572 A | 9/1998 | Loveall | |
| 5,813,981 A * | 9/1998 | Carim | 600/372 |
| 6,719,713 B2 | 4/2004 | Mason | |
| 6,736,855 B2 | 5/2004 | Bertels | |
| 2003/0013999 A1 * | 1/2003 | Grelsamer | 602/24 |

(Continued)

OTHER PUBLICATIONS

Dictionary Defintion for "durable".*

(Continued)

*Primary Examiner* — Thomas J Sweet
*Assistant Examiner* — Marcia Hoffman
(74) *Attorney, Agent, or Firm* — Baker Botts L.L.P.

(57) ABSTRACT

Anchoring system for a cable-activated prosthetic or orthotic device includes a fastener comprising a base and a clasp-engaging member, wherein the fastener further comprises an adhesive to secure the base directly to skin of a wearer; and a clasp comprising a first end configured to engage and rotate about the clasp-engaging member and a second end configured to engage the activation cable of a prosthetic or orthotic device. Also included is a prosthetic or orthotic system that includes the anchoring system in combination with a prosthetic or orthotic device comprising an activation cable and a terminal device, wherein the activation cable comprises a first end operatively coupled to the terminal device and a second end engaged with the second end of the clasp.

14 Claims, 10 Drawing Sheets

U.S. PATENT DOCUMENTS

| | | | |
|---|---|---|---|
| 2003/0093158 A1 | 5/2003 | Phillips et al. | |
| 2004/0138763 A1 | 7/2004 | Perkins et al. | |
| 2005/0277859 A1* | 12/2005 | Carlsmith | 602/20 |
| 2007/0032884 A1 | 2/2007 | Veatch | |
| 2007/0106187 A1 | 5/2007 | Campbell et al. | |

OTHER PUBLICATIONS

Dictionary Definition for "flange".*
Pierson, An overview of skin contact applications for pressure-sensitive adhesives, Tappi Journal, Jun. 1990.*
U.S. Appl. No. 11/787,161 (Abandoned), filed Apr. 13, 2007.
U.S. Appl. No. 11/787,161, Oct. 26, 2010 Final Office Action.
U.S. Appl. No. 11/787,161, Jan. 27, 2010 Applicant Summary of Interview with Examiner.
U.S. Appl. No. 11/787,161, Dec. 28, 2009 Examiner Interview Summary.
U.S. Appl. No. 11/787,161, Nov. 25, 2009 Response to Non-Final Office Action.
U.S. Appl. No. 11/787,161, Jun. 26, 2009 Non-Final Office Action.
Cambridge Online Dictionary, definition "harness", accessed Oct. 20, 2010.
Merriam Webster Online Dictionary, definition "Harness", accessed Oct. 19, 2010.
Brunnstrom, "Shoulder Region", Clinical Kinesiology, 3rd Edition, Chapter 5, F.A. Davis Company, Philadelphia, 1972.
Collier et al., "Axilla bypass ring for shoulder harness for upper-limb prothesis", Journal of Prosthetics and Orthotics, 8(4): 130-131, 1996.
Crandall et al., "Pediatric unilateral below-elbow amputees: retrospective analysis of 34 patients given multiple prosthetic options", J Pediatr Orthop, 22(3): 380-383, 2002.
Curran et al., "The prosthetic treatment of upper limb defiency", Prosthet Orthot Int., 15(2): 82-87, 1997.
Fryet et al., "Upper-limb prosthetics/body-powered components", Atlas of Limb Prosthetics: Surgical, Prothetic, and Rehabilation Principles, Mosby, 2nd Edition, chapter 6A, pp. 107-131, 1992.
Fryet et al., "Upper-limb prosthetics/body-powered components", Atlas of Limb Prosthetics: Surgical, Prothetic, and Rehabilation Principles, Mosby, 2nd Edition, chapter 6B, pp. 133-150, 1992.
Kejlaa, "Consumer concerns and the functional value of protheses to upper limb amputees", prosthet Orthot Int., 17(3): 157-163, 1993.
Krebs et al., "Prosthetic management of children with limb deficiencies", Phys ther., 71(12): 934, 1991.
Krebs et al., "acceptability of the NYU No. 1 child-sized body powered hand", arch Phys Med Rehabil., 69(2): 137-141, 1998.
Kuyper et al., "Prosthetic management of children in the Netherlands with upper limb deficiencies", Prosthet Orthot int., 25(3): 228-234, 2001.
Meeks et al., "evaluation of a new design: Body-powered, upper-limb prosthesis without shoulder harness", Journal of Prosthetics and Orthostics, 1(1): 45-49, 1989.
Postema et al., "Prosthesis rejection in children with a unilateral congenital arm defect", Clin. Rehabil., 13(3): 243-249, 1999.
Roninger, "Study finds chronic pain in fact of life amputess", Biomechanics, 13(1): 15-16, 2006.
Roth-Isigkeit et al., "pain among children and adolescents: Restriction in daily living and triggering factors", Pediatrics, 115(2): 125-162, 2005.
Shaperman et al., "is body powered operation of upper limb protheses feasible for young limb deficient children?", Prosthet. Orthot. Int., 19(3): 165-175, 1995.
The International Search Report and Written Opinion dated Dec. 12, 2007 from Internationa Application No. PCT/US07/66862.

* cited by examiner

-- Prior Art --

FIG. 4A

-- Prior Art --

FIG. 4B

-- Prior Art --

FIG. 4C

-- Prior Art --

ANCHORING SYSTEM FOR PROSTHETIC AND ORTHOTIC DEVICES

CROSS REFERENCE TO RELATED APPLICATIONS

This application is a continuation of U.S. patent application Ser. No. 11/787,161, filed Apr. 13, 2007, now abandoned which claims priority to U.S. Patent Application Ser. No. 60/793,178, filed on Apr. 19, 2006, the entire contents of each of which are incorporated by reference herein, and from each of which priority is claimed

TECHNICAL FIELD

This invention relates to prosthetic and orthotic devices.

BACKGROUND

Various limb prosthesis and orthotic devices have been designed that require a harness system for their operation. However, the benefits of prostheses and orthotic devices are diminished by the harness system in that it can cause user discomfort, reduced cosmesis due to pulling on clothing, and in the case of upper limb prostheses or orthotic devices, poor posturing of the shoulders, shoulder muscle asymmetry, and perceived pain in the contralateral shoulder, arm, and hand due, e.g., to impingement of axillae. Further, the function of a prosthetic or orthotic device with a harness system is often limited in that contralateral body power is needed to operate a terminal device affixed to the prothetic or orthotic device.

SUMMARY

The present application provides a novel anchoring system that can replace the typical harness system used with cable-activated prosthesis and orthotic systems. Use of the anchoring system with a prosthetic or orthotic device can eliminate many of the problems associated with using a harness system.

Accordingly, in one aspect, the application provides an anchoring system. The anchoring system can include (i) a fastener comprising a base and a clasp-engaging member; and (ii) a clasp, comprising a first end configured to engage and rotate about the clasp-engaging member and a second end configured to engage an activation cable of a prosthetic or orthotic device.

In another aspect, the application provides a prosthetic or orthotic system. The system can include (a) an anchoring system that includes (i) a fastener comprising a base and a clasp-engaging member; and (ii) a clasp comprising a first end configured to engage and rotate about the clasp-engaging member and a second end engaged with an activation cable of a prosthetic or orthotic device; and (b) a prosthetic or orthotic device comprising an activation cable and a terminal device, wherein the activation cable comprises a first end operatively coupled to the terminal device and a second end engaged with the second end of the clasp.

The base and clasp engaging member can together be a unitary structure. Alternatively, the clasp engaging member can be detachably connected to the base. The clasp-engaging member can be flange, button, or knob that protrudes from a portion of the base, e.g., from about the center axis of the base.

The base can be a flat member that includes an adhesive side adapted to adhere the base to the body of a wearer of the device, and a non-adhesive side. The base can be any shape, e.g., circular, rectangular, square, or triangular in shape. The base can include a thermoplastic material, e.g., a perforated thermoplastic material. The fastener can also include a thermoplastic material. The clasp can be any functional shape, e.g., a loop or hook structure.

The anchoring system can further include a linker between the clasp and the activation cable, and can be adjustable to accommodate different sizes of wearers, lengths of prosthetic or orthotic devices, and lengths of activation cables. The linker can include a cloth material, such as a canvas strap.

The prosthetic or orthotic system can include a prosthetic device, e.g., a prosthetic arm, such as a below elbow forearm prosthesis, or a prosthetic leg. The prosthetic device can include a prehensile terminal device, such as a prosthetic hand or hook. Alternatively, the prosthetic or orthotic system can include an orthotic device, e.g., a dynamic splint, such as a dynamic hand, forearm, elbow or leg splint.

In yet another aspect, the application provides a method of securing a prosthetic or orthotic device to a wearer. The method includes (a) providing a prosthetic or orthotic system described herein; (b) attaching the prosthetic or orthotic device to a limb of the wearer; (c) adhering the fastener to the upper back of the wearer; and (d) engaging the clasp and clasp-engaging member; to thereby connect the activation cable to the fastener and assemble the prosthetic or orthotic device on the wearer.

Unless otherwise defined, all technical and scientific terms used herein have the same meaning as commonly understood by one of ordinary skill in the art to which this invention belongs. Although methods and equipment similar or equivalent to those described herein can be used in the practice of the present invention, suitable methods and equipment are described below. All publications and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features and advantages of the invention will be apparent from the description and drawings, and from the claims.

DETAILED DESCRIPTION

The application provides an anchoring system for cable-activated prosthetic and orthotic devices. The new anchoring system enables the user to activate the cable-activated prosthetic or orthotic device's terminal device, e.g., by applying tension to the cable using scapulo-thoracic movement, without the aid of a harness system, and thus avoids the problems associated with such harness systems.

The application also provides a prosthetic or orthotic system that includes the anchoring system, as well as methods for securing such a system to a wearer.

Figure 1:
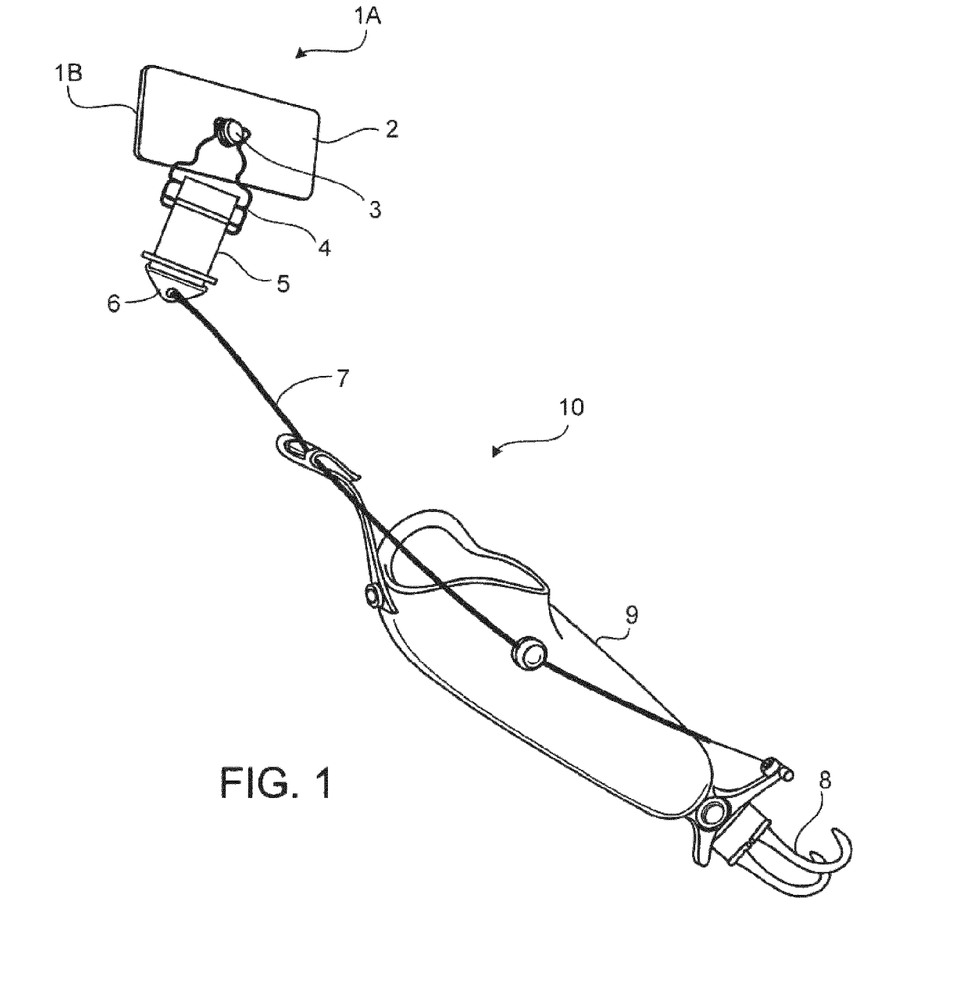
FIG. 1 is a perspective view of a prosthetic device with an exemplary assembled anchoring system.

FIG. 1 provides an overview of an exemplary assembled prosthetic system 10 and an exemplary anchoring system 1A.

The anchoring system includes, as its main components, a fastener 1B comprising a base 2 and a clasp-engaging member 3, and a clasp 4. The system optionally includes a linker 5. In FIG. 1, linker 5 is connected to an activation cable 7 through a ball joint 6 between the two, such that the entire anchoring system is pivotably connected to a second end of activation cable 7. Activation cable 7 is connected at a first end to a terminal device 8, in this case a hook, mounted on a prosthetic device 9. In certain embodiments, clasp 4 can be configured to directly engage activation cable 7 of prosthetic or orthotic device 9, and linker 5 can be excluded.

Figure 2:
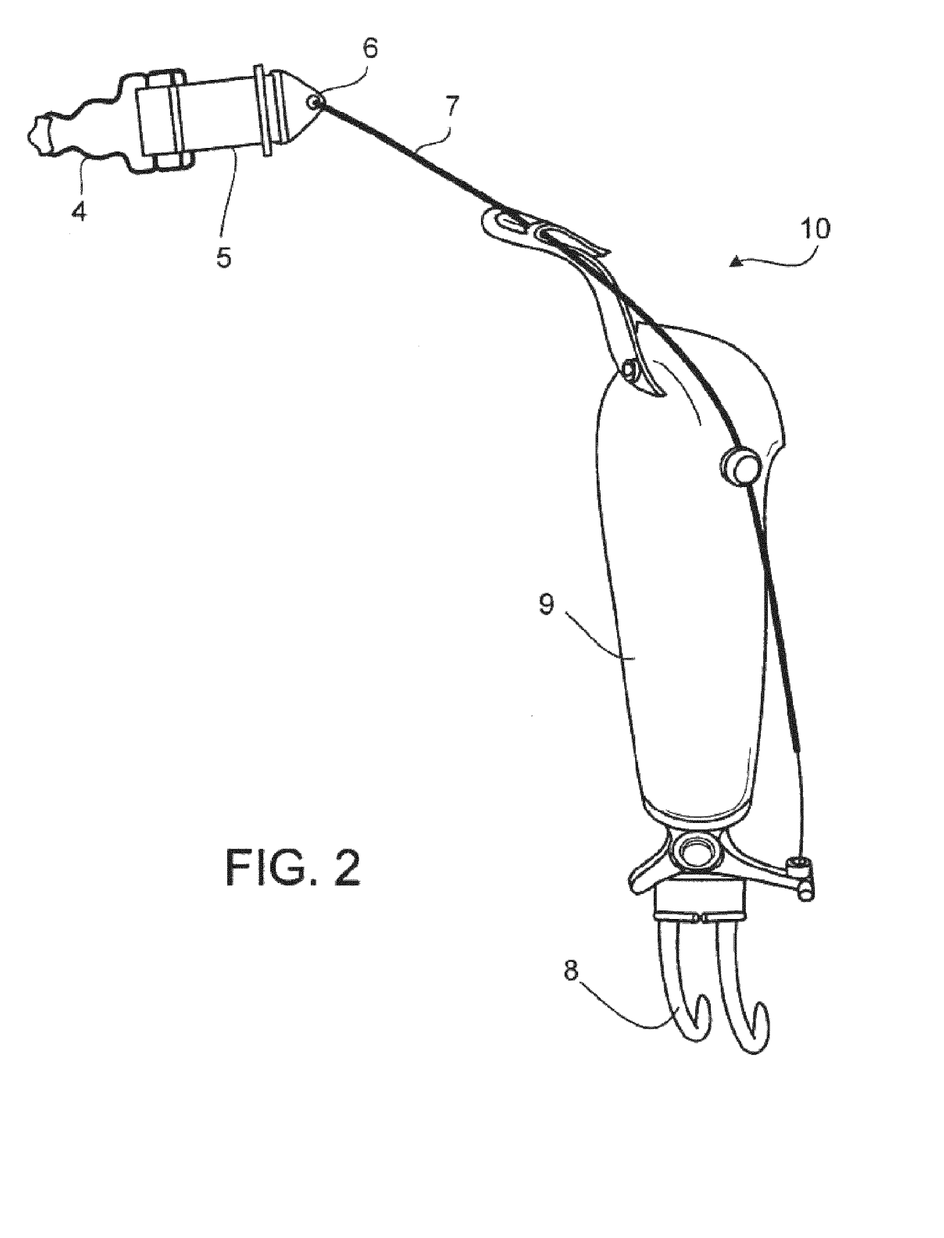
FIG. 2. is a perspective view of the prosthetic device depicted in FIG. 1 in a unassembled state.
Figure 3A:
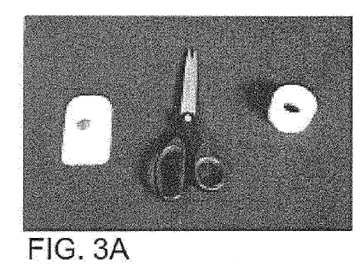
FIGS. 3A-3G illustrate assembly of an exemplary fastener.
Figure 3B:
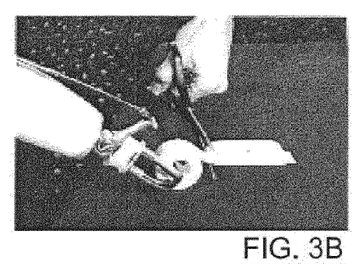
Figure 3C:
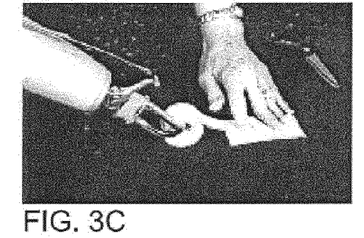
Figure 3D:
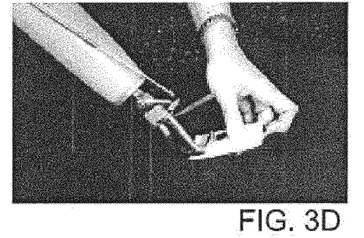
Figure 3E:
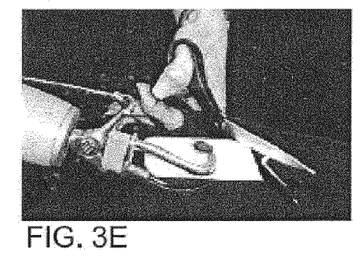
Figure 3F:
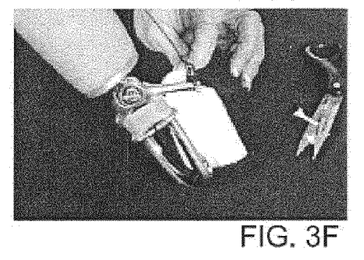
Figure 3G:
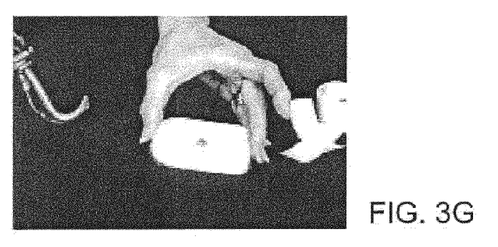

FIG. 2 provides a slightly different perspective of the exemplary system depicted in FIG. 1 in an unassembled state. Clasp 4 is disengaged from clasp engaging member 3. Fastener 1B is not shown in FIG. 2.

Fastener 1B can be a unitary structure, i.e., clasp engaging member 3 and base 2 can be formed as a single unit, and optionally including the same material, e.g., a thermoplastic material. Alternatively, base 2 and clasp engaging member 3 can be formed as separable units. In such embodiments, base 2 and clasp engaging member 3 can include the same or different materials.

Where base 2 and clasp-engaging member 3 are separable units, base 2 and clasp-engaging member 3 can be connected using any method known to those of skill in the art, e.g., riveting or bonding (e.g., gluing). Alternatively or in addition, base 2 can be constructed with a perforation configured such that it can receive clasp-engaging member 3 therethrough and hold clasp-engaging member 3 in position optionally with or without using other means. Base 2 can also be constructed with a perforation to accommodate embodiments wherein clasp-engaging member 3 is separable from base 2 and attached (reversibly or irreversibly) to clasp 4, and wherein the system is assembled by inserting clasp engaging member 3 into a perforation in base 2.

Base 2 can be constructed as a flat sheet of material, e.g., a patch. The flat sheet of material can be formed into any shape and size desirable to a skilled practitioner, including, inter alia, a circle, square, rectangle, triangle or octagon. Base 2 can be a solid sheet of material or have one or more perforations, e.g., to enhance air flow through base 2 to the wearer's skin. Skilled practitioners will appreciate that it can be made of any material useful in such applications, e.g., a fabric, thermoplastic material, or metal, or a mixture thereof. For example, the base can be made of a perforated thermoplastic material, e.g., AQUAPLAST-T™.

Base 2 can include an adhesive on at least one side, which can be used to adhere fastener 1A to the skin of the wearer. The adhesive can be any adhesive known in the art, e.g., an adhesive acceptable for use on a wearer's skin. For example, the adhesive can be a medical glue or a tape (e.g., a double sided tape such as toupee tape).

Clasp-engaging member 3 can be any member that is suitable for use as a connection point between base 2 and clasp 4. In certain embodiments, clasp-engaging member 3 is a button (e.g., a so-called "bachelor button"), knob, or flange. Skilled practitioners will appreciate that clasp-engaging member can be made of any rigid material, e.g., a thermoplastic material or metal, e.g., steel, aluminum or titanium.

Clasp 4 is depicted in FIG. 1 and FIG. 2 as a typical clothing (e.g., "overalls")-type clasp. However, skilled practitioners will appreciate that many variations on this theme are possible. For example, clasp 4 can be a simple hook or loop structure, configured at one end to connect with clasp-engaging member 3 and at the other end to connect with linker 5 or directly with activation cable 7, such that linker 5 can be excluded. Clasp 4 can be made of any material, e.g., a metal (e.g., steel or titanium) or thermoplastic material.

Linker 5 is optionally included in the system and can be any material, e.g., a cloth, such as canvass, metal, or thermoplastic material. Linker 5 can be adjustable in length, e.g., to accommodate, inter alia, different sizes of wearers, lengths of prosthetic or orthotic devices, etc.

Anchoring system 1A can be used with any cable-activated prosthesis or orthotic device. The prosthetic device 9 shown in FIG. 1 and FIG. 2 is a below elbow forearm prosthesis with a modified Muenster socket with a terminal hook. However, skilled practitioners will appreciate that many other cable-activated prosthetic and orthotic devices for upper and lower limbs are known and commercially available, as are other terminal devices. For example, anchoring system 1A can be used with a prosthesis that replaces the entire arm and/or that include a prosthetic hand or other prehensile device. As another example, with regard to orthotic devices, anchoring system 1A can be used with a dynamic splint, e.g., a dynamic hand, forearm, or elbow splint. The system can also be used with lower limb prostheses and orthotic devices. For example, the system can be used with a cable-activated prosthetic leg or a dynamic leg (e.g., knee) splint.

The system is suitable for use with any population, child or adult, having a condition (congenital or acquired) that benefits from the use of a cable-activated prosthetic or orthotic device. For example, it can be used in those having a below elbow upper limb deficiency, spinal cord injury, brachial plexus palsy, cerebral palsy with hemiplegia, head trauma, or hand trauma, among many others.

The invention will be further described in the following examples, which do not limit the scope of the invention defined by the claims.

Example 1

Construction of an Exemplary Fastener and Use Thereof

FIGS. 3A-3G illustrate the assembly of an exemplary fastener. Assembly in this instance requires a perforated thermoplastic material, such as AQUAPLAST-T™, a bachelor button (e.g., a Dritz® bachelor button) fastened through and held approximately in the center by the perforated thermoplastic material (see FIG. 3A). A double sided tape, such as toupee tape, was cut to roughly the size of the perforated thermoplastic material (see FIGS. 3B-3D). The double sided tape was trimmed from the perforated thermoplastic material (see FIG. 3E). The backing was then removed from the double sided tape to yield a fastener prepared for use (see FIGS. 3F-3G).

Figure 4A:
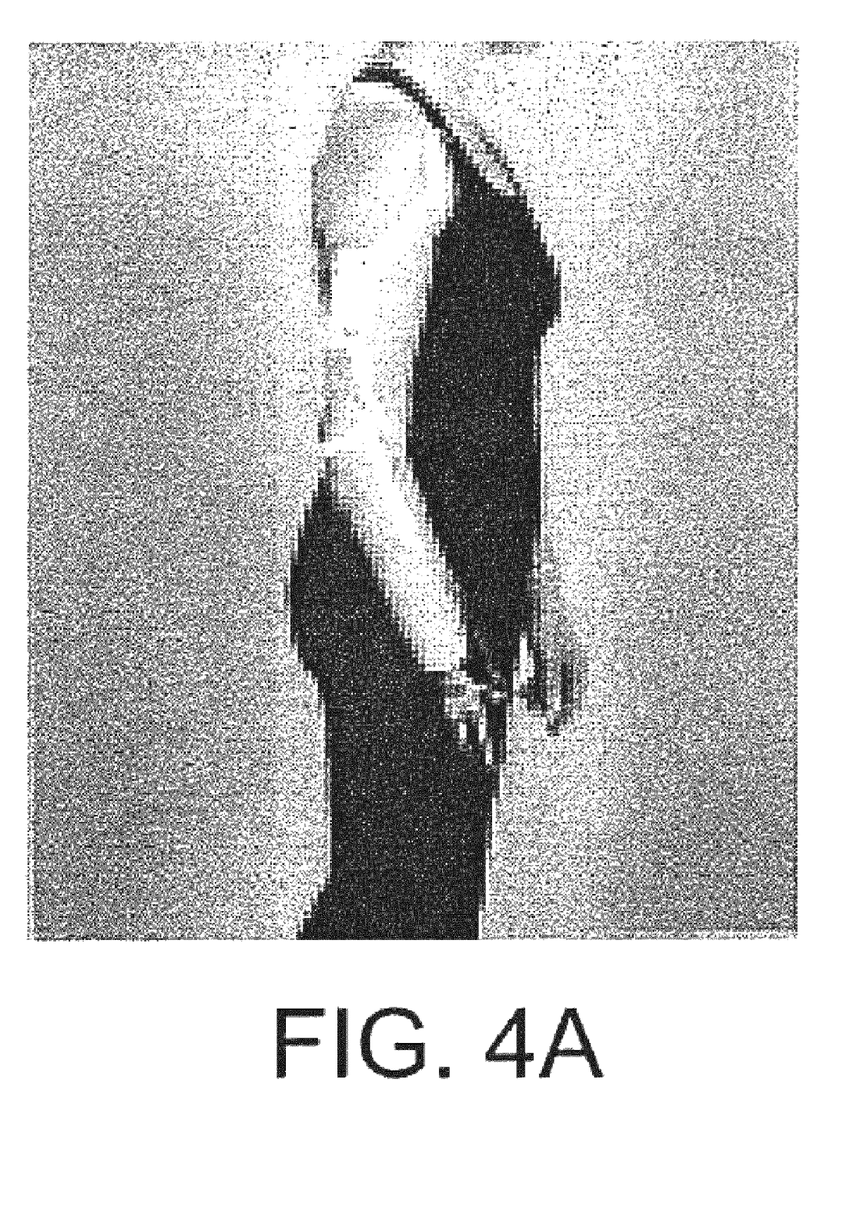
FIGS. 4A-4D illustrate the use of a "Figure of 8" harness system by a wearer of a prosthesis.
Figure 4B:
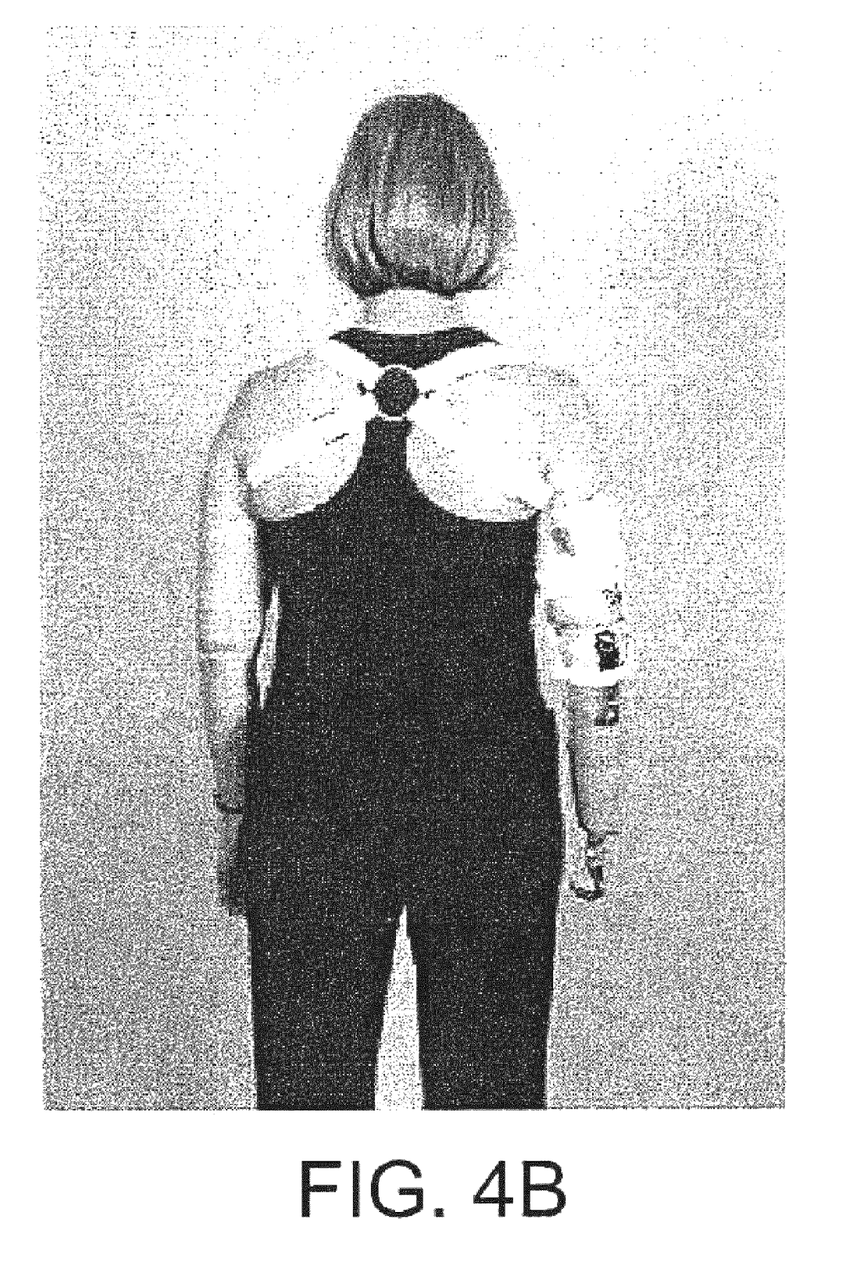
Figure 4C:
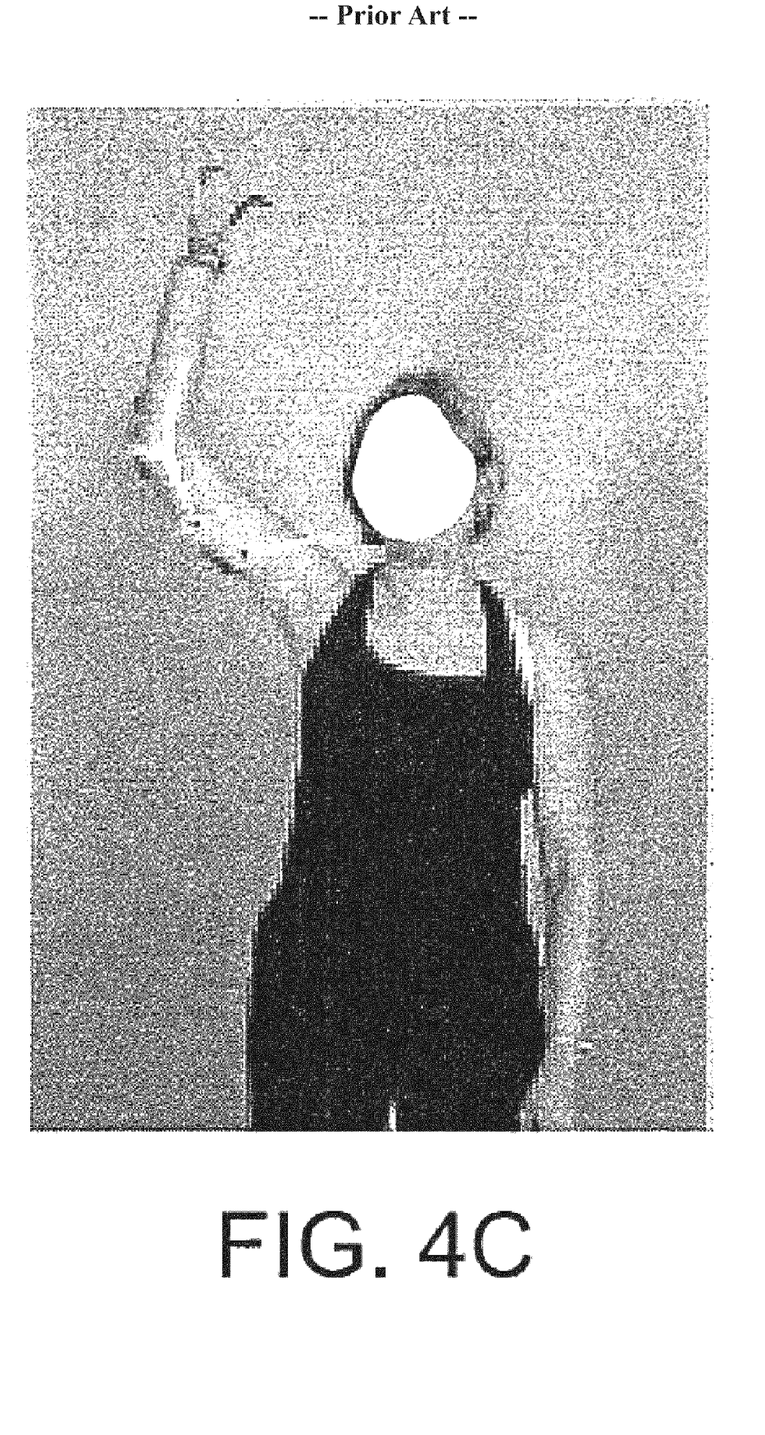
Figure 4D:
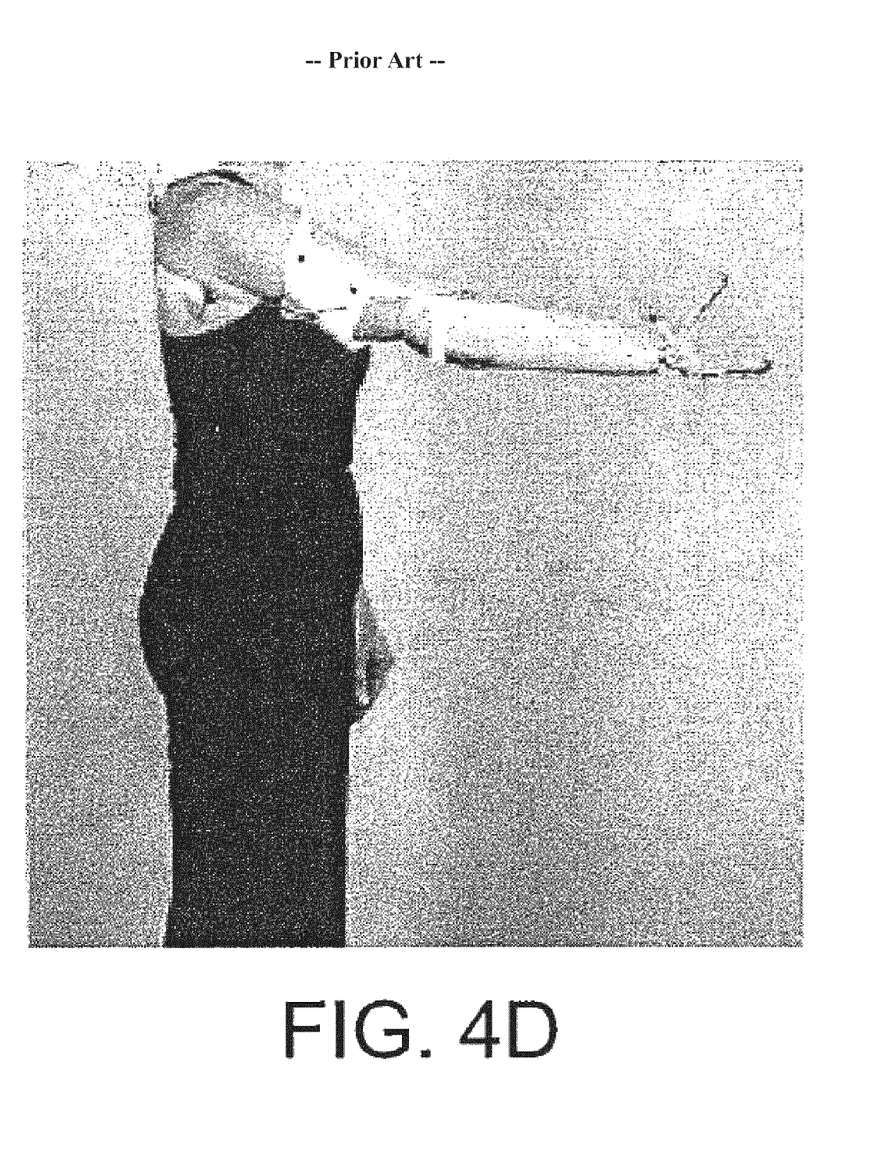

For the purposes of contrasting the embodiment demonstrated in the present Example with prior art systems, FIGS. 4A-4D are presented. These figures illustrate the use of a prior art system—a so-called "Figure of 8" harness system. FIG. 4A is a side view of a wearer of the harness system. FIG. 4B is a back view of a wearer of the harness system. FIG. 4C is a frontal view of a wearer of the harness system, with arm and prosthesis extended above the head. Note how one of the harness straps inconveniently lifts off of and above the right shoulder of the wearer. FIG. 4D is a side view of the wearer with arm extended and prehensile hook in open position.

Figure 5A:
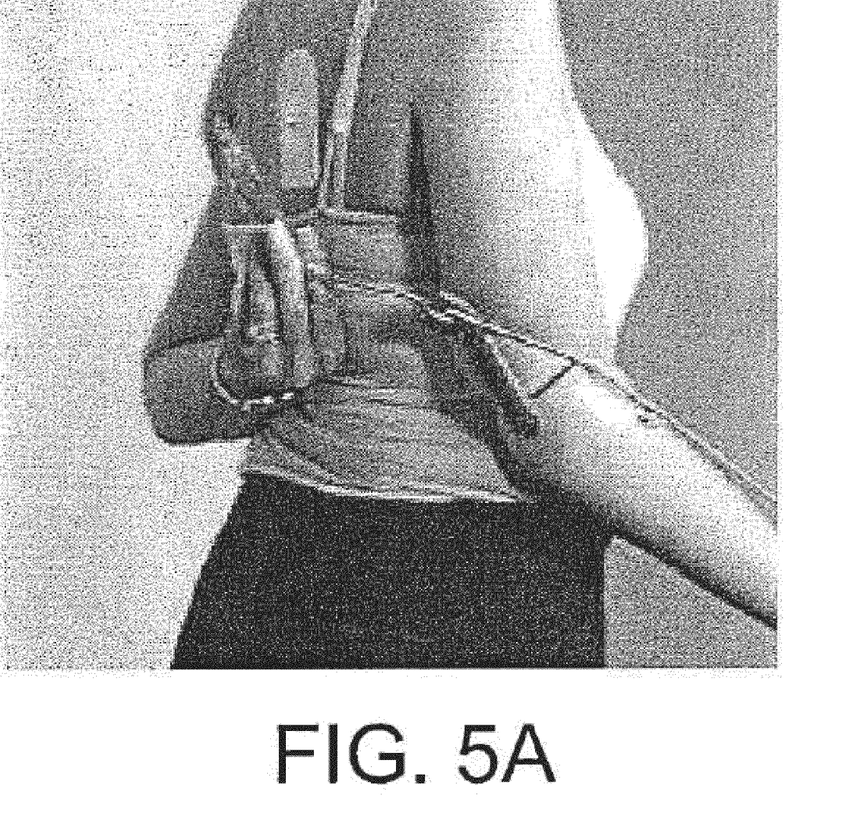
FIGS. 5A-5C illustrate the use of an exemplary anchoring system by a wearer of a prosthesis.
Figure 5B:
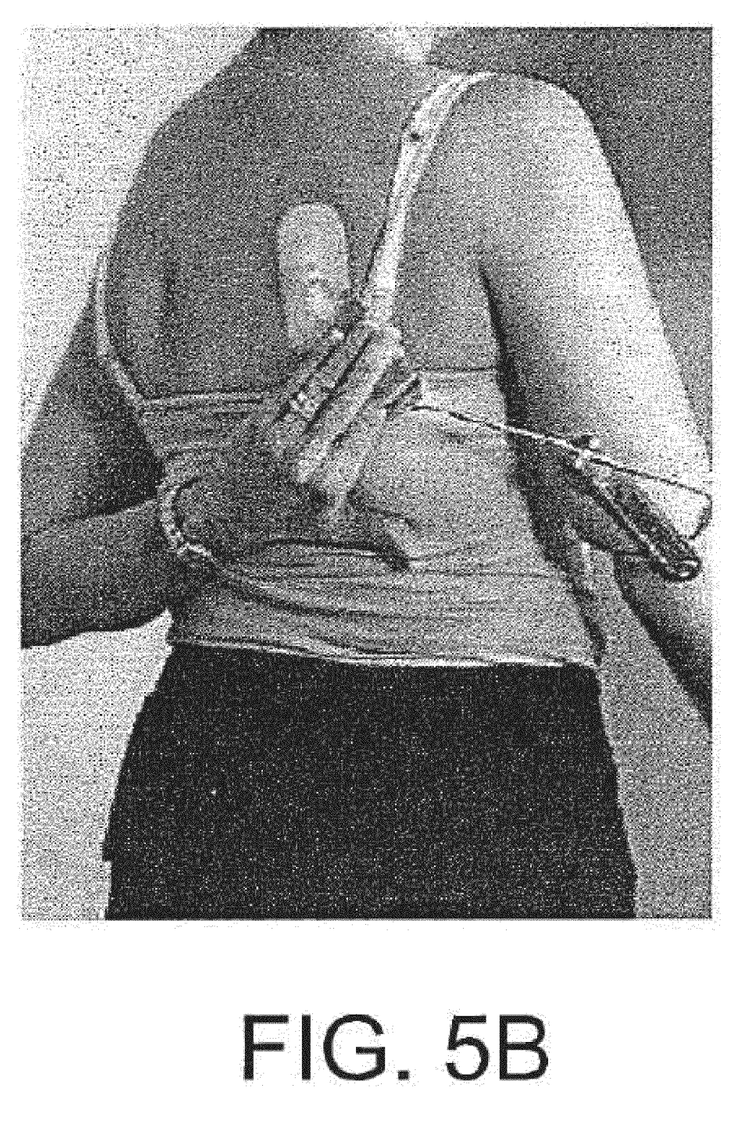
Figure 5C:
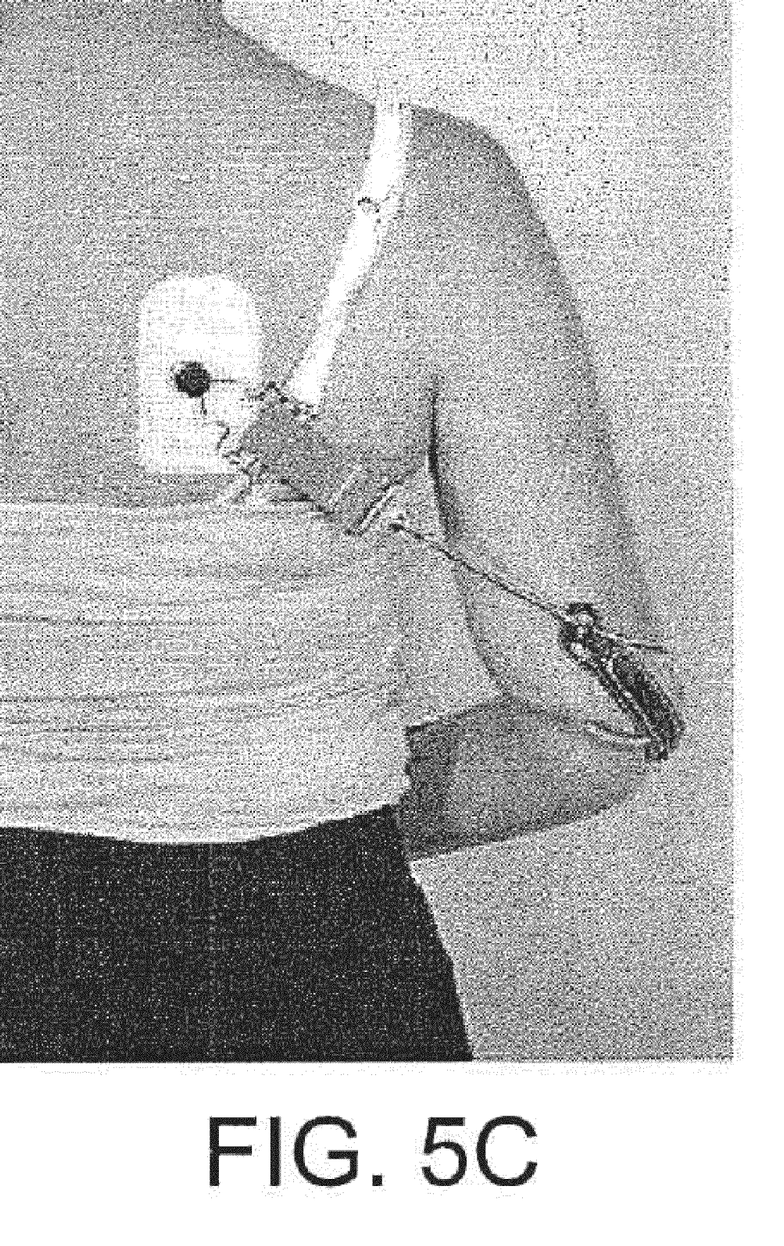

FIGS. 5A-5C illustrate the use of an exemplary anchoring system prepared in part in a procedure similar to that outlined above in FIGS. 3A-3G. Specifically, FIGS. 5A-5C illustrate assembly of a prosthetic system of the present invention on a wearer. FIGS. 5A-5C are side view of a wearer with a elbow forearm prosthesis with a modified Muenster socket and a prehensile hook. The fastener was affixed to the wearer's skin just medial to the scapula and slightly above the level of the axilla (see FIG. 5A). The wearer with his/her opposite hand, grasped the clasp and/or linker attached to the activation cable and engaged (e.g., hooked) the clasp with the clasp-engaging member (FIG. 5B). Upon engagement, the device was fully assembled and activated (FIG. 5C).

A number of embodiments of the invention have been described. Nevertheless, it will be understood that various modifications may be made without departing from the spirit and scope of the invention. For Accordingly, other embodiments are within the scope of the following claims.

What is claimed is:

1. A prosthetic or orthotic system, comprising:
   (a) an anchoring system including:
      (i) a fastener including a substantially planar base, and a clasp-engaging member protruding from a portion of the base and having an outwardly-extending flange, the fastener further including an adhesive suitable to secure the base directly to skin of a wearer, and
      (ii) a clasp having a first end configured to engage and rotate about the clasp-engaging member and a second end configured to engage a cable of a prosthetic or orthotic device; and
   (b) a prosthetic or orthotic device at least including a cable and a terminal device, the cable having a first end coupled to the terminal device and a second end coupled with the second end of the clasp,
   wherein the adhesive has a sufficient strength to support manual operation of the prosthetic or orthotic device.

2. The system of claim 1, wherein the base is made of a thermoplastic a material selected from the group consisting of thermoplastic material, a fabric, a metal and a mixture thereof.

3. The system of claim 1, wherein the adhesive is a double sided tape.

4. The system of claim 1, wherein the prosthetic or orthotic device is configured for ipsilateral placement with the fastener of the anchoring system.

5. The system of claim 1, wherein the cable is an activation cable for the prosthetic or orthotic device.

6. The system of claim 5, wherein the activation cable is operatively coupled to the terminal device.

7. The system of claim 1, wherein the prosthetic or orthotic device is a prosthetic device.

8. The system of claim 7, wherein the prosthetic device is a prosthetic arm.

9. The system of claim 8, wherein the prosthetic device is a below elbow forearm prosthesis.

10. The system of claim 1, wherein the terminal device is a prehensile device.

11. The system of claim 10, wherein the prehensile device is a prosthetic hand or a hook.

12. The system of claim 1, wherein the prosthetic or orthotic device is an orthotic device.

13. The system of claim 12, wherein the orthotic device is a dynamic splint.

14. The system of claim 1, further comprising a linker between the clasp and the cable.

* * * * *